(12) United States Patent
Dumas

(10) Patent No.: US 6,185,750 B1
(45) Date of Patent: Feb. 13, 2001

(54) PORTABLE COOLING DEVICE

(76) Inventor: Dexter Reginald Dumas, 3934 Sautee Trail, Conley, GA (US) 30288

( * ) Notice: Under 35 U.S.C. 154(b), the term of this patent shall be extended for 0 days.

(21) Appl. No.: 09/511,502

(22) Filed: Feb. 23, 2000

Related U.S. Application Data

(60) Provisional application No. 60/121,516, filed on Feb. 23, 1999.

(51) Int. Cl.[7] .......................................... A42B 1/24
(52) U.S. Cl. .......................... 2/209.13; 2/209.12; 2/171.2
(58) Field of Search ............................. 2/209.12, 209.13, 2/175.1, 195.1, 171.2; 607/110, 109

(56) References Cited

U.S. PATENT DOCUMENTS

| | | | |
|---|---|---|---|
| 1,910,328 | * 5/1933 | Glennan | 607/110 |
| 4,641,655 | * 2/1987 | Abt | 128/380 |
| 4,980,928 | * 1/1991 | Ellis | 2/88 |
| 5,247,928 | * 9/1993 | Stilts | 607/109 |
| 5,327,585 | * 7/1994 | Karlan | 2/7 |
| 5,542,128 | * 8/1996 | Lomas | 2/173 |
| 5,694,648 | * 12/1997 | Nucifora | 2/172 |
| 5,860,165 | * 1/1999 | Cvijanovich | 2/195.1 |
| 6,029,278 | * 2/2000 | Lopez | 2/209.13 |

\* cited by examiner

*Primary Examiner*—Bibhu Mohanty
(74) *Attorney, Agent, or Firm*—Goldstein & Canino

(57) ABSTRACT

A portable cooling device that is easily fitted around the user's neck. The cooling device comprises a pouch with an interior portion and a fastening means that securely fits it around the user's neck. The cooling device is provided with a cap attachment means that allow securement of the cooling device to the user's cap. The pouch is filled with ice that cools the air around the user to provide a cool sensation.

5 Claims, 1 Drawing Sheet

PORTABLE COOLING DEVICE

CROSS REFERENCES AND RELATED SUBJECT MATTER

This application relates to subject matter contained in provisional patent application Ser. No. 60/121,516, filed in the United States Patent Office on Feb. 23, 1999.

BACKGROUND OF THE INVENTION

The invention relates to an apparatus that allows individuals to cool themselves. More particularly, the invention relates to an inexpensive and portable cooling device that allows individuals to remain cool while working in hot temperatures.

It is generally known that strenuous work in hot weather conditions can cause harmful effects on one's health. It is also known that a person's work efficiency is inversely impacted by temperature, since heat causes mental and physical fatigue. As a result, as the temperature in the workplace gets hotter, the productivity of the workers decreases. Unfortunately, it is difficult for people who work outdoors to keep themselves cool, while performing their work assignments.

There are occasions when one is required to perform physically strenuous work, which raises the body temperature and results in heavy perspiration that can cause dehydration. While it is possible to maintain cooler temperatures in an indoor workplace, it is difficult to ensure low temperatures while working outdoors.

Many people wear caps or wide-rim hats to shield themselves from direct sunlight while working outdoors. Unfortunately, head gear merely blocks direct contact of sunlight with one's skin, while failing to ensure cooler temperatures. Thus, it is desirable to provide a mechanism that allows people to keep themselves cool, while working in high temperatures.

While the prior art units may be suitable for the particular purpose employed, or for general use, they would not be as suitable for the purposes of the present invention as disclosed hereinafter.

SUMMARY OF THE INVENTION

It is an object of the invention to provide an apparatus that allows a person to remain cool while working in high temperatures.

It is another object of the present invention to provide a portable cooling device that is easy to use and allows one to remain cool. Accordingly, the present invention provides a cooling device that comprises a pouch with ice stored therein. The cooling device has a pair of securement wings that are secured together around the user's neck, such that the cooling device provides a cool sensation to the upper portion of the user's body.

To the accomplishment of the above and related objects the invention may be embodied in the form illustrated in the accompanying drawings. Attention is called to the fact, however, that the drawings are illustrative only. Variations are contemplated as being part of the invention.

BRIEF DESCRIPTION OF THE DRAWINGS

The above and other aspects, features and advantages of the present invention will be more apparent from the following detailed description thereof, which is presented in conjunction with the following drawings, wherein corresponding reference characters indicate corresponding components throughout the drawing figures.

DETAILED DESCRIPTION OF THE PREFERRED EMBODIMENTS

Figure 1:
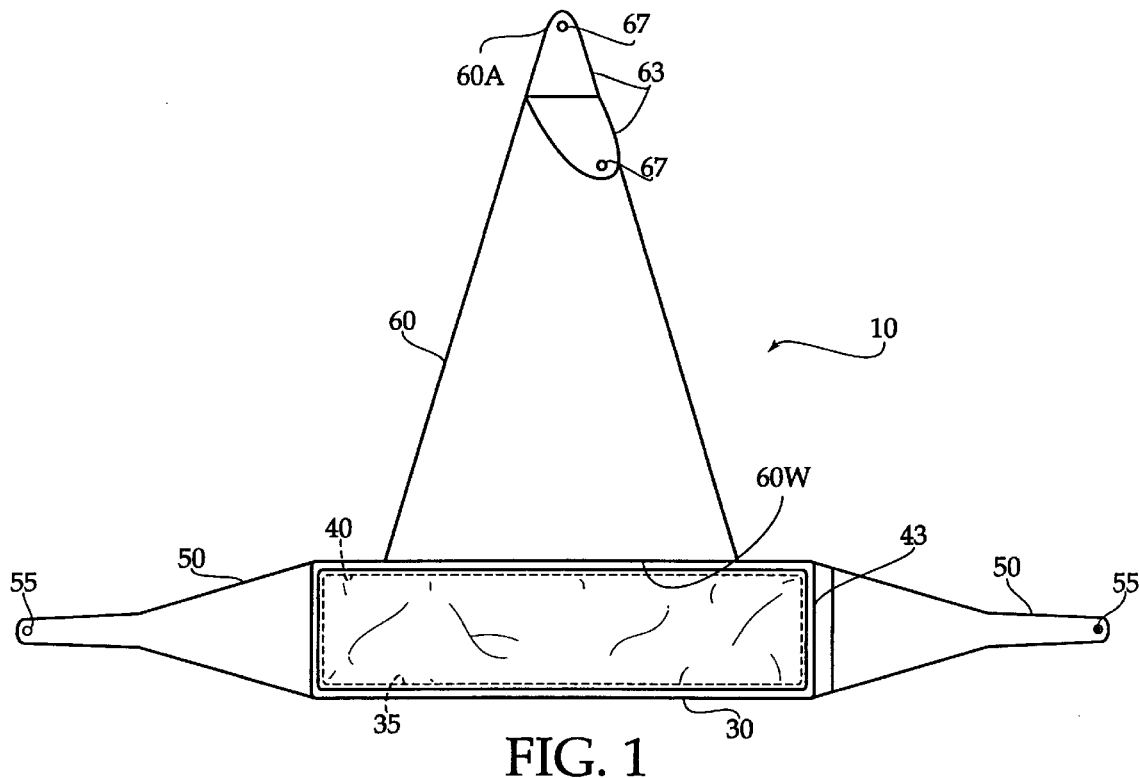
FIG. 1 provides a diagrammatic perspective view of the cooling device, in accordance with the present invention.

FIG. 1 shows a cooling device 10 that may be detachably fitted around a user's neck.

The cooling device comprises a pouch 30 that has an interior portion 35 therein. The pouch 30 is constructed from a flexible material, such as rubber, soft plastic or cloth to ensure easy bending of the pouch so that the cooling device 10 readily fits around the user's neck. The interior portion 35 is preferably provided with a removable water-proof bag 40, which has a sealing mechanism 43. According to another embodiment, the interior portion 35 has a water-proof lining.

Figure 2:
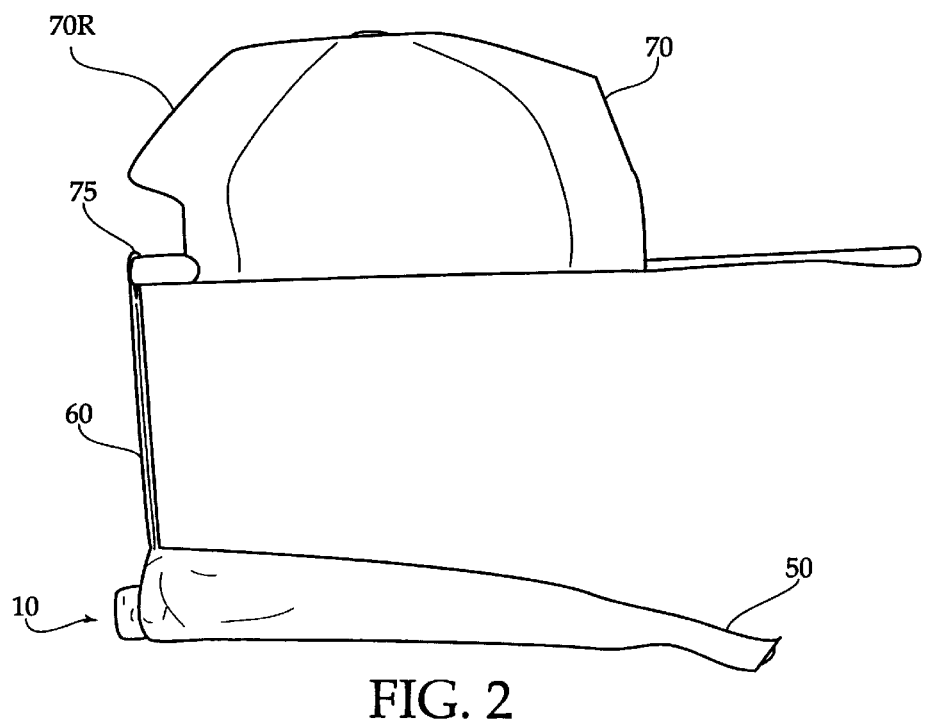
FIG. 2 provides a side elevational view of the cooling device fitted around the user's neck.

The cooling device 10 is provided with a pair of securement wings 50 that are attached to the pouch 30. The securement wings 50 allows the user to securely fit the cooling device 10 around his neck, as shown in FIG. 2. The securement wings 50 are provided with snaps 55 that engage therebetween to securely affix the pair of securement wings 50 to each other. The securement wings are generally tapered from the pouch toward the straps to provide an optimum fit around the individual's neck.

The cooling device 10 is provided with a cap attachment device 60 to allow securement of the cooling device 10 to a cap 70 worn by the user. The cap attachment device 60 is triangular in shape, having a wide base 60W which corresponds to the pouch 30, and an apex 60A. As is well known, the typical cap 70 comprises an adjustment strap 75 at its rear 70R to allows users to adjust the cap 70 to accommodate users having different size heads. At the apex 60A, the cap attachment means 60 is split into a pair of flaps 63 that secure the cooling device 10 to the adjustment strap 75 of the cap 70. To facilitate securement of the attachment means 60 to the adjustment strap 75 of the cap 70, the flaps 63 are provided with mating snap buttons 67 that are mateable to secure the flaps 63 together around the cap adjustment strap 75. Accordingly, the cap attachment device 60 is made from two fabric layers which are substantially the same size, extend parallel to each other, and are laminated together except at the apex 60A where the two layers split to form the flaps 63.

According to the invention, the interior portion 35 of the pouch 30 is generally filled with ice, which cools the entire cooling device 10. The cooling device 10 reduces the temperature of the air in its immediate surroundings, and conducts heat directly from the individual wearing the cooling device 10, which provides a cool sensation to the user.

In conclusion, herein is presented a cooling device which attaches around the neck of an individual, and attaches to a cap worn by that individual, to provide a cooling effect to that individual. Many specific details contained in the above description merely illustrate some preferred embodiments and should not be construed as a limitation on the scope of the invention. Accordingly, many other variations are possible within the spirit of the present invention.

What is claimed is:

1. A portable cooling device, for use by an individual having a neck and wearing a cap, the cap having a cap rear and having an adjustment strap at the cap rear, comprising:

a pouch, the pouch having an internal pocket capable of containing ice and containing moisture produced therefrom, the pouch having a sealing mechanism for selectively allowing access to the internal pocket and selectively sealing the internal pocket to make said internal pocket water impervious;

a pair of securement wings, extending from the pouch in opposite directions, such that the wings and the pouch are together capable of extending fully around the neck of the individual, the securement wings having snaps which are capable of engaging each other for connecting the securement wings to each other and thereby securing the cooling device around the neck of the individual; and a cap attachment device, substantially triangular in shape having a base and an apex, made of two layers, both substantially the same in size, both layers laminated to each other except at the apex where the layers split from each other to form a pair of flaps, the flaps having snap buttons capable of securing the flaps to each other, the base attached to the pouch such that the cap attachment device extends upward from the pouch and the flaps are attachable around the cap adjustment strap to secure the cooling device to the cap of the individudal.

2. A portable cooling device, for use by an individual having a neck and wearing a cap, the cap having a cap rear and having an adjustment strap at the cap rear, comprising:

a pouch, the pouch having an internal pocket capable of containing ice and containing moisture produced therefrom;

a pair of securement wings, extending from the pouch in opposite directions, such that the wings and the pouch are together capable of extending fully around the neck of the individual and securing thereat; and a cap attachment device being triangular in shape having a base and an apex, the base attached to the pouch, the apex attachable around the cap adjustment strap, said cap attachment device extends upward from the pouch and attaches around the cap adjustment strap to secure the cooling device to the cap of the individual.

3. The portable cooling device as recited in claim 2, wherein the cap attachment device is constructed from two fabric layers laminated to each other except at the apex where the layers split to form two flaps, each flap having a snap button which is mateable to the other to secure the flaps around the cap adjustment strap.

4. The portable cooling device as recited in claim 3, wherein the securement wings have snaps which are capable of engaging each other for connecting the securement wings to each other and thereby securing the cooling device around the neck of the individual.

5. The portable cooling device as recited in claim 4, wherein the pouch has a sealing mechanism for selectively allowing access to the internal pocket and selectively sealing the internal pocket to make said internal pocket water impervious.

* * * * *